US010856792B2

United States Patent
Wei et al.

(10) Patent No.: US 10,856,792 B2
(45) Date of Patent: Dec. 8, 2020

(54) URINARY SYMPTOM MANAGEMENT

(71) Applicant: Medtronic, Inc., Minneapolis, MN (US)

(72) Inventors: Xuan K. Wei, Minnetonka, MN (US); Linnea Burman, Hopkins, MN (US); Timothy J. Denison, Minneapolis, MN (US); Nnamdi Njoku, Eden Prairie, MN (US); Maren Bean, Los Angeles, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 350 days.

(21) Appl. No.: 15/902,606

(22) Filed: Feb. 22, 2018

(65) Prior Publication Data

US 2019/0254582 A1 Aug. 22, 2019

(51) Int. Cl.
*A61B 5/00* (2006.01)
*A61B 5/20* (2006.01)
(Continued)

(52) U.S. Cl.
CPC .......... *A61B 5/202* (2013.01); *A61B 5/14507* (2013.01); *A61B 5/207* (2013.01);
(Continued)

(58) Field of Classification Search
CPC ..... A61B 5/202; A61B 5/207; A61B 5/14507; G16H 10/40; G16H 10/60; G16H 40/67; G16H 50/20
See application file for complete search history.

(56) References Cited

U.S. PATENT DOCUMENTS 5,062,304 A 11/1991 Van Buskirk et al.
5,369,600 A 11/1994 Ito et al.
(Continued)

FOREIGN PATENT DOCUMENTS

CN 201312699 Y 9/2009
CN 201536911 U 8/2010
(Continued)

OTHER PUBLICATIONS

Copeland,"New App Turns Your iPhone into a Mobile Urine Lab," wired.com, Feb. 26, 2013, 4 pp.
(Continued)

*Primary Examiner* — Max F Hindenburg
(74) *Attorney, Agent, or Firm* — Patterson Thuente Pedersen, P.A.

(57) ABSTRACT

Systems, devices, and techniques are disclosed for predicting a urinary event of a patient. In one example, a system comprises a fluid consumption cup comprising one or more sensors. The system may comprise communication circuitry configured to receive, from the fluid consumption cup, one or more signals that indicate an amount of fluid removed from the fluid consumption cup. The system may comprise processing circuitry configured to: update a patient log based on the one or more signals that indicate the amount of fluid removed from the fluid consumption cup; determine that the urinary event is predicted to occur, the occurrence of the urinary event predicted based on the patient log; and provide, in response to the determination and for receipt by the patient, a notification that the urinary event is predicted to occur.

30 Claims, 7 Drawing Sheets

(51) Int. Cl.
  *A61B 5/145* (2006.01)
  *G16H 10/40* (2018.01)
  *G16H 50/20* (2018.01)
  *G16H 10/60* (2018.01)
  *G16H 40/63* (2018.01)
  *G16H 40/67* (2018.01)
  *G16B 40/00* (2019.01)

(52) U.S. Cl.
  CPC ............ *G16H 10/40* (2018.01); *G16H 10/60* (2018.01); *G16H 40/63* (2018.01); *G16H 40/67* (2018.01); *G16H 50/20* (2018.01); *G16B 40/00* (2019.02)

(56) References Cited

U.S. PATENT DOCUMENTS

| | | | |
|---|---|---|---|
| 5,495,854 | A | 3/1996 | Currie |
| 6,235,010 | B1 | 5/2001 | Wilkinson et al. |
| 6,372,951 | B1 | 4/2002 | Ter-Ovanesyan et al. |
| 6,479,727 | B1 | 11/2002 | Roe |
| 6,557,484 | B1 | 5/2003 | Engelman |
| 6,627,152 | B1 | 9/2003 | Wong |
| 6,716,393 | B2 | 4/2004 | Lappe et al. |
| 7,040,139 | B2 | 5/2006 | Sunshine |
| 7,522,061 | B2 | 4/2009 | Rondoni et al. |
| 7,855,653 | B2 | 12/2010 | Rondoni et al. |
| 7,977,529 | B2 | 7/2011 | Bergman et al. |
| 8,141,420 | B2 | 3/2012 | Hirao |
| 8,299,930 | B2 | 10/2012 | Schmid-Schonbein et al. |
| 8,421,636 | B2 | 4/2013 | Collette et al. |
| 8,455,257 | B2 | 6/2013 | Lappe et al. |
| 8,496,604 | B2 | 7/2013 | Brohan et al. |
| 8,567,258 | B2 | 10/2013 | Belotserkovsky |
| 8,986,613 | B2 | 3/2015 | Cohen |
| 9,212,067 | B2 | 12/2015 | Gellibolian et al. |
| 9,283,123 | B2 | 3/2016 | Lewis et al. |
| 9,740,824 | B2 | 8/2017 | Chang et al. |
| 2005/0247121 | A1 | 11/2005 | Pelster |
| 2006/0278156 | A1 | 12/2006 | Miller |
| 2007/0225666 | A1 | 9/2007 | Otto |
| 2011/0149693 | A1 | 6/2011 | Liao |
| 2013/0157232 | A1 | 6/2013 | Ehrenkranz |
| 2013/0289886 | A1 | 10/2013 | Ricks |
| 2014/0303790 | A1 | 10/2014 | Huang et al. |
| 2015/0024349 | A1* | 1/2015 | Bischoff ................ A47G 23/16 434/127 |
| 2016/0025545 | A1* | 1/2016 | Saltzgiver ............ G01F 23/263 73/304 C |
| 2016/0166096 | A1* | 6/2016 | DiMaria-Ghalili .... G06Q 50/24 702/19 |
| 2017/0067770 | A1 | 3/2017 | Sun |
| 2017/0293846 | A1* | 10/2017 | Zyglowicz ................ G06K 9/62 |

FOREIGN PATENT DOCUMENTS

| | | |
|---|---|---|
| CN | 201861646 U | 6/2011 |
| CN | 202730908 U | 2/2013 |
| CN | 203016500 U | 6/2013 |
| CN | 103217198 A | 7/2013 |
| CN | 203587598 U | 5/2014 |
| WO | 2014145971 A2 | 9/2014 |
| WO | WO 2015/017702 A2 | 2/2015 |
| WO | 2015175969 A1 | 11/2015 |
| WO | WO 2017/132067 A2 | 8/2017 |

OTHER PUBLICATIONS

Dickey, "This Amazing New 'Smart Cup' Can Tell What Kind of Drink is Inside It," Business Insider, Jun. 12, 2014, 5 pp.

PCT International Search Report and Written Opinion for International Application No. PCT/US2019/016227 dated Apr. 30, 2019, 12 pages.

* cited by examiner

URINARY SYMPTOM MANAGEMENT

TECHNICAL FIELD

This disclosure generally relates to diagnostic medical systems.

BACKGROUND

Bladder dysfunction, such as urgency (overactive bladder) or urinary incontinence, is a problem that may afflict people of all ages, genders, and races. Various muscles, nerves, organs, and conduits within the pelvic floor cooperate to collect, store, and release urine. A variety of disorders may compromise urinary tract performance, and contribute to urgency or urinary incontinence. Many of the disorders may be associated with aging, injury, or illness. Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence. Nerves running though the pelvic floor may stimulate contractility in the sphincter. An improper communication between the nervous system and the urethra or urinary sphincter may result in a bladder dysfunction, such as urgency (overactive bladder), urge incontinence, or another type of urinary incontinence.

SUMMARY

This disclosure describes systems, devices, and techniques for managing symptoms of urinary incontinence, overactive bladder, or other urinary conditions. Patients with overactive bladder may have sudden urges to urinate and may experience involuntary voiding (i.e., urge incontinence). Some treatments for overactive bladder may include behavioral strategies, such as fluid schedules, timed voiding and bladder-holding techniques using pelvic floor muscles. However, these behavioral strategies may be insufficient for managing symptoms of some patients.

In accordance with one or more techniques of this disclosure, a system may be configured to automatically log patient fluid intake, predict the occurrence of urinary events based on the logged fluid intake, and provide warnings of impending urinary events. The system includes a cup that measures an amount of fluid consumed by a patient and/or an amount of fluid voided by the patient. Based on the amount of fluid consumed and/or voided by the patient, the system may predict and notify the patient of the occurrence of future urinary events. By notifying the patient of a predicted occurrence of future events, the patient may be also to visit a bathroom with sufficient warning time; hence eliminate a potential urgency or incontinence episode.

In general, a urinary event as described herein may include a urinary voiding event, a urinary urgency event, a urinary incontinence event, a urinary leak event, or any other type of urinary event.

In an example, a method for predicting a urinary event of a patient may comprise receiving one or more signals correlated to fluid removal from a fluid consumption cup; updating a patient log based on the one or more signals correlated to fluid removal; determining that a urinary event for a patient is predicted to occur based on the patient log; and providing an indication that the urinary event (e.g. urgency or urinary voiding event) is predicted to occur.

In an example, a fluid consumption cup may comprise a fluid consumption cup body configured to store a fluid; one or more sensors configured to sense fluid removal from the fluid consumption cup; a power source coupled to the one or more sensors; processing circuitry, coupled to the power source and the one or more sensors, the processing circuitry configured to predict a urinary event of a patient and provide a notification that the urinary void is predicted to occur in response to the one or more sensors sensing fluid removal from the fluid consumption cup.

In an example, a fluid consumption cup includes one or more sensors configured to sense fluid removal from the fluid consumption cup; and processing circuitry. In this example, the processing circuitry is configured to determine, based on signals generated by the one or more sensors, an amount of fluid consumed by a patient; determine an occurrence of a urinary event of the patient predicted based on the amount of fluid consumed by the patient; and output, based on a time difference between a current time and a time at which the urinary event is predicted to occur, a notification of the urinary event.

In some examples, the one or more sensors may be used to track symptoms and improve technique predictability (e.g., algorithm predictability) over time. In some examples, the prediction of the urinary event may be used as an input, such as for adjusting therapy.

In an example, a mobile computing device for predicting a urinary event of a patient may comprise communication circuitry configured to receive, from a fluid consumption cup, one or more signals correlated to a patient's fluid state; processing circuitry configured to: determine the fluid state of the patient based on the one or more signals; update a patient log based on the determined fluid state; determine that the urinary event is predicted to occur based on the patient log; and provide an indication that the urinary void is predicted to occur in response to the determination.

The details of one or more examples of the techniques of this disclosure are set forth in the accompanying drawings and the description below. Other features, objects, and advantages of the techniques will be apparent from the description and drawings, and from the claims.

DETAILED DESCRIPTION

In some aspects, the systems and techniques described herein include automatically logging fluid intake of a patient, predicting an occurrence of a future urinary event based on the logged fluid intake, and warning the patient of the predicted urinary event. Additional aspects include titrating therapies related to overactive bladder based on the automatically logged fluid intake. Therapy titration may include oral drug dosing adjustment, neuromodulation programming or real-time therapy changes, and adjustable mechanical support therapies.

A fluid consumption cup (e.g., a smart cup) may sense fluid intake information of a patient. The sensed information may be stored locally in the cup, or exported out via wired or wireless communications to an external device such as a mobile computing device used by the patient (e.g., a smartphone) or a remote server.

The cup may predict potential symptom onset based on the fluid intake information. For instance, the cup may predict that a urinary event is likely to occur at a particular time, or a time window that is meaningful for the patient in the future. The algorithm may also provide the probability of an episode occurring within a set time window. Based on predicting the onset of potential symptoms, the cup or a connected mobile application may provide a warning to the patient in order to enable the patient to take action to avoid or otherwise mitigate the potential symptoms. For instance, in response to determining that a urinary event is predicted to occur at a particular time, the cup may output a warning in advance of the particular time. In this way, the techniques of this disclosure may enable the patient to plan for the void (e.g., get to a bathroom).

Figure 1:
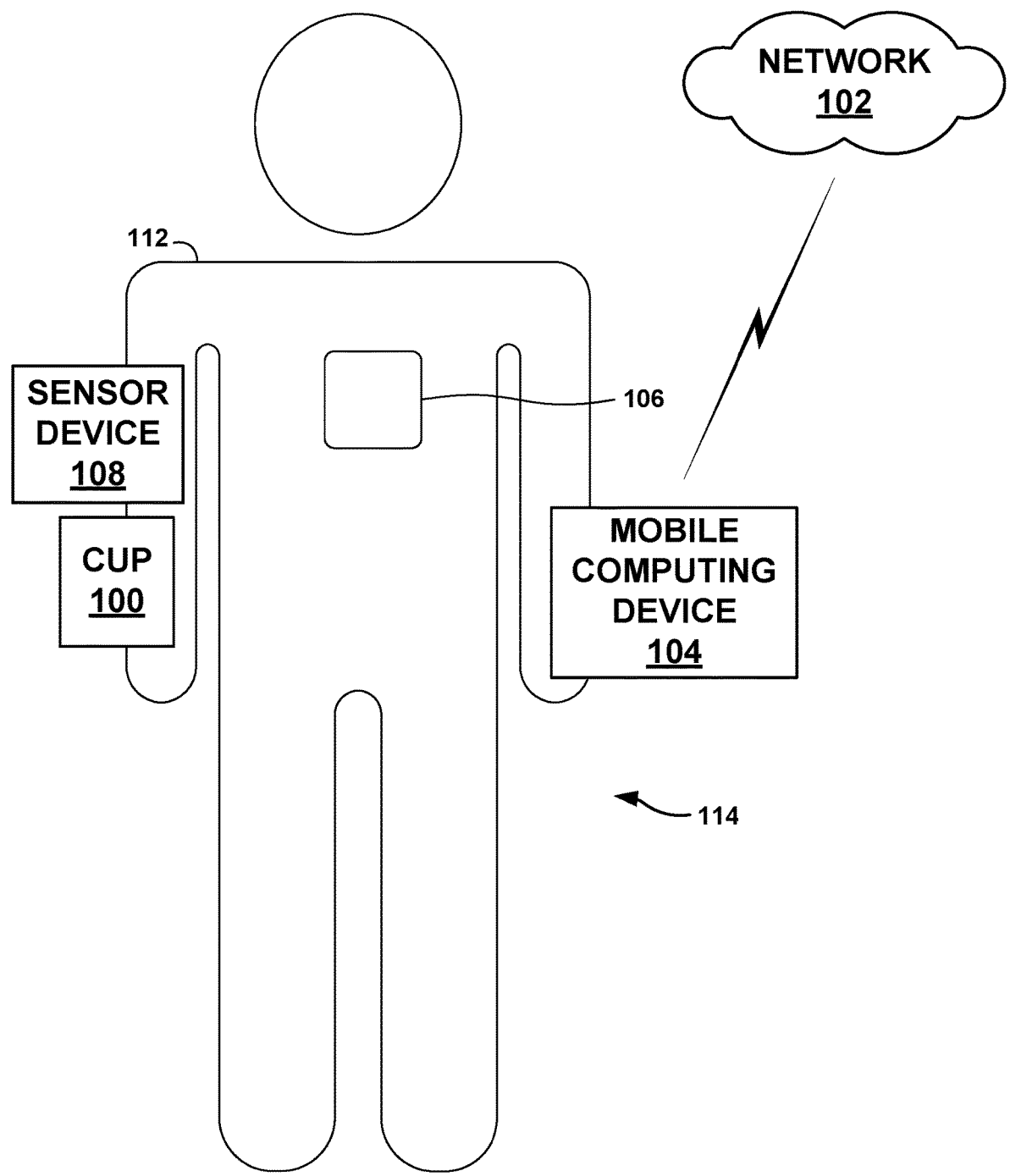
FIG. 1 is a conceptual diagram illustrating an example system configured to predict a urinary event of a patient according to an example of the techniques of the disclosure.

FIG. 1 is a conceptual diagram illustrating an example system 114 configured for predicting a urinary event of a patient according to an example of the techniques of the disclosure. System 114 may include a cup 100, a network 102, a mobile computing device 104, a medical device 106 (e.g., an implantable medical device "IMD") that may be implanted in or secured to patient 112, and a sensor device 108. Although a wireless communication link is illustrated between network 102 and mobile computing device 104, any element of system 114 may be configured to communicate with any other device in system 114. Details of one example of system 114 where various elements of system 114 communicate with each other are discussed below with reference to FIG. 2.

Cup 100 is a fluid consumption cup configured to generate data indicative of an amount of fluid consumed by patient 112. For instance, cup 100 may include one or more sensors that measure an amount of fluid that flows through a lid of cup 100. Cup 100 may store the generated data locally in a patient log. Additionally or alternatively, cup 100 may output the generated data to an external device, such as mobile computing device 104. Additional details of one example of cup 100 are discussed below with reference to FIG. 3.

System 114 may include mobile computing device 104, which may be a computing device configured to facilitate one or more of the tracking of fluid consumption data, the prediction of urinary events, and the warning of patient 112 of the predicted urinary events. For instance, mobile computing device 104 may update a patient log based on signals received from cup 100 that indicate an amount of fluid removed from cup 100. Mobile computing device 104 may predict, based on the patient log, when a urinary event is likely to occur and provide patient 112 with a commensurate warning. For instance, in response to determining that a urinary event is predicted to occur at a particular time, mobile computing device 104 may output a notification to the user in advance of the particular time. Example warnings that may be provided include, but are not limited to, flashing lights, vibrations, graphical warnings displayed on a screen of mobile computing device 104, or the like. Additional details of one example of mobile computing device 104 are discussed below with reference to FIG. 4.

While described above as being performed by mobile computing device 104, the updating of the patient log, prediction of symptom onset, and warning of the patient may be performed by various devices of system 114. As one example, all of the updating/predicting/warning may be performed by cup 100. As another example, cup 100 may perform the updating/predicting and mobile computing device 104 may perform the warning. As another example, a remote server (e.g., remote device 124 of FIG. 2) may perform the updating/predicting and mobile computing device 104 or cup 100 may perform the warning.

Medical device 106 may be a bladder control therapy device. For example, medical device 106 may be configured to provide electrical stimulation to nerves that control the bladder of patient 112 to help the bladder function more normally. For example, medical device 106 may be configured to provide percutaneous tibial nerve stimulation therapy for treating overactive bladder and the associated symptoms of frequency, urgency, and urinary urge incontinence. In some examples, medical device 106 may be a mechanical medical device configured to address stress urinary incomitance. Additional details of one example of medical device 106 are discussed below with reference to FIG. 5.

System 114 may comprise sensor device 108, which in some examples, may comprise a fitness tracker, such as may be configured to track physical activity of patient 112. One or more of cup 100, sensor device 108, and mobile computing device 104 may be configured to sense activity of patient 112. For example, sensor device 108 may track perspiration of patient 112. Sensor device 108 may transmit time-stamped patient perspiration information signals to communication circuitry 390, and processing circuitry 380 may update patient log 350 with the patient perspiration information. In some examples, one or both of cup 100 and mobile computing device 104 comprises sensor device 108.

Figure 2:
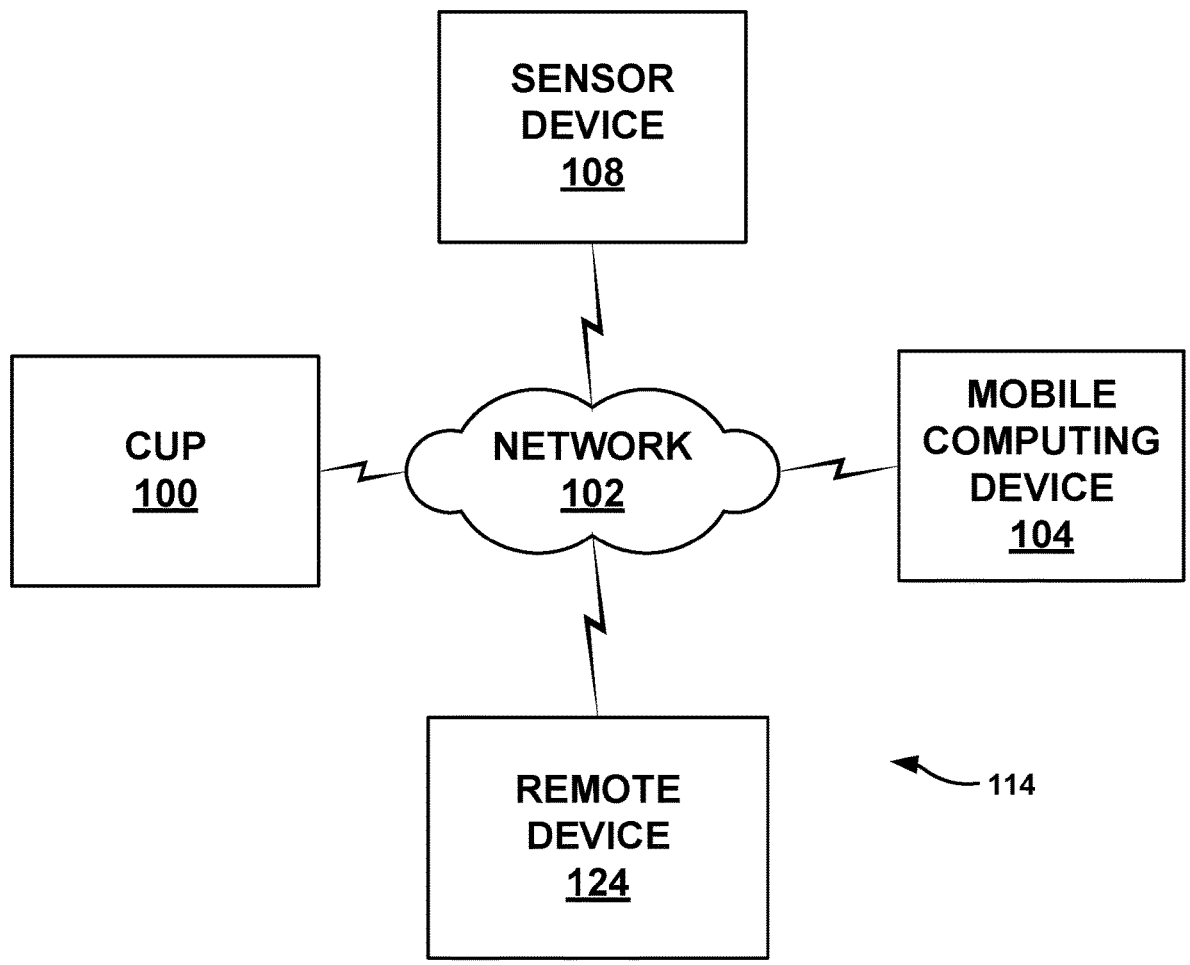
FIG. 2 is a conceptual diagram of the example system of FIG. 1 that predicts a urinary event of a patient according to an example of the techniques of the disclosure.

FIG. 2 is a conceptual diagram of one example of system 114. In the example of FIG. 2, cup 100, mobile computing device 104, sensor device 108, and remote device 124 (e.g., a server) are each communicatively coupled to network 102. Network 102 may represent any single network or combination of networks that facilitate communication between devices. As one example, network 102 may represent a Bluetooth link between cup 100 and mobile computing device 104. As another example, network 102 may represent a combination of wireless and wired networks that form a link between remote device 124 and mobile computing device 104 (e.g., the internet).

In an example, remote device 124 may comprise a secure storage site for information that has been collected from any other device in system 114. Patient 112 or a health care provider may use one or more mobile computing devices (e.g., mobile computing device 104) or other access points to securely access stored data on remote device 124. Any device described herein may be coupled to a remote patient monitoring system, such as Carelink®, available from Medtronic plc, of Dublin, Ireland.

In some examples, fluid intake sensors of cup 100 may work in conjunction with a software application on mobile computing device 104 that also tracks patient symptoms, such as may include logging time stamps of incontinence episodes (e.g., leaks), voids, and urgency episodes, as well as the severity of urge. These symptoms can be entered manually by patients or tracked automatically via sensors (such as sound of voiding or toilet flushing, and vicinity to a known bathroom location), or prompted by sensors and confirmed by the patient.

In some examples, the systems and techniques described herein may include monitoring voids of the patients. The patient may void into a voiding cup (e.g., that may comprise similar electronics elements as fluid consumption cup 100), such as may be configured to determine voided volume, urine acidity, bacteria content, sugar content, or other chemical content related to bladder health. The voiding cup may be portable and washable (e.g., or may comprise a disposable liner). The voiding cup may also allow urine flowing out of the cup into the toilet during voiding, such as may include an inlet opening and an outlet port. In some examples, the systems and techniques described herein may be implemented into a diaper that may include sensors. The tracked symptoms can be used as input for a learning algorithm that optimize prediction over time specific to patient's sensor and symptom patterns.

Therapy titration may include titrating oral drug dosing, neuromodulation programming (e.g., pre-programmed or real-time therapy adjustment), or adjusting mechanical support therapies. Although chiefly described with respect to urinary incontinence and disease states that are sensitive to fluid intake (e.g., urgency, and frequency, urinary retention, fecal incontinence, constipation, pelvic pain flare up, irritable bowel syndrome, diabetes, obesity, and other metabolic syndrome), the subject matter described herein may also be applicable to other diseases states. By using the systems and techniques described herein, patient behavior tracking may be automated, symptom control may be increased by predicting symptom onset and allowing for greater warning time for patient action, and may provide better information for therapy titration. In some examples, patient compliance may be increased by using the subject matter of this disclosure (e.g., the automatically updated patient log or the event prediction techniques) relative to conventional patient logs (e.g., pen and paper diary logs), which may be relatively subjective and cumbersome to maintain. The systems and techniques described herein may also supplement or enhance patient behavior modification or dietary modification.

Figure 3:
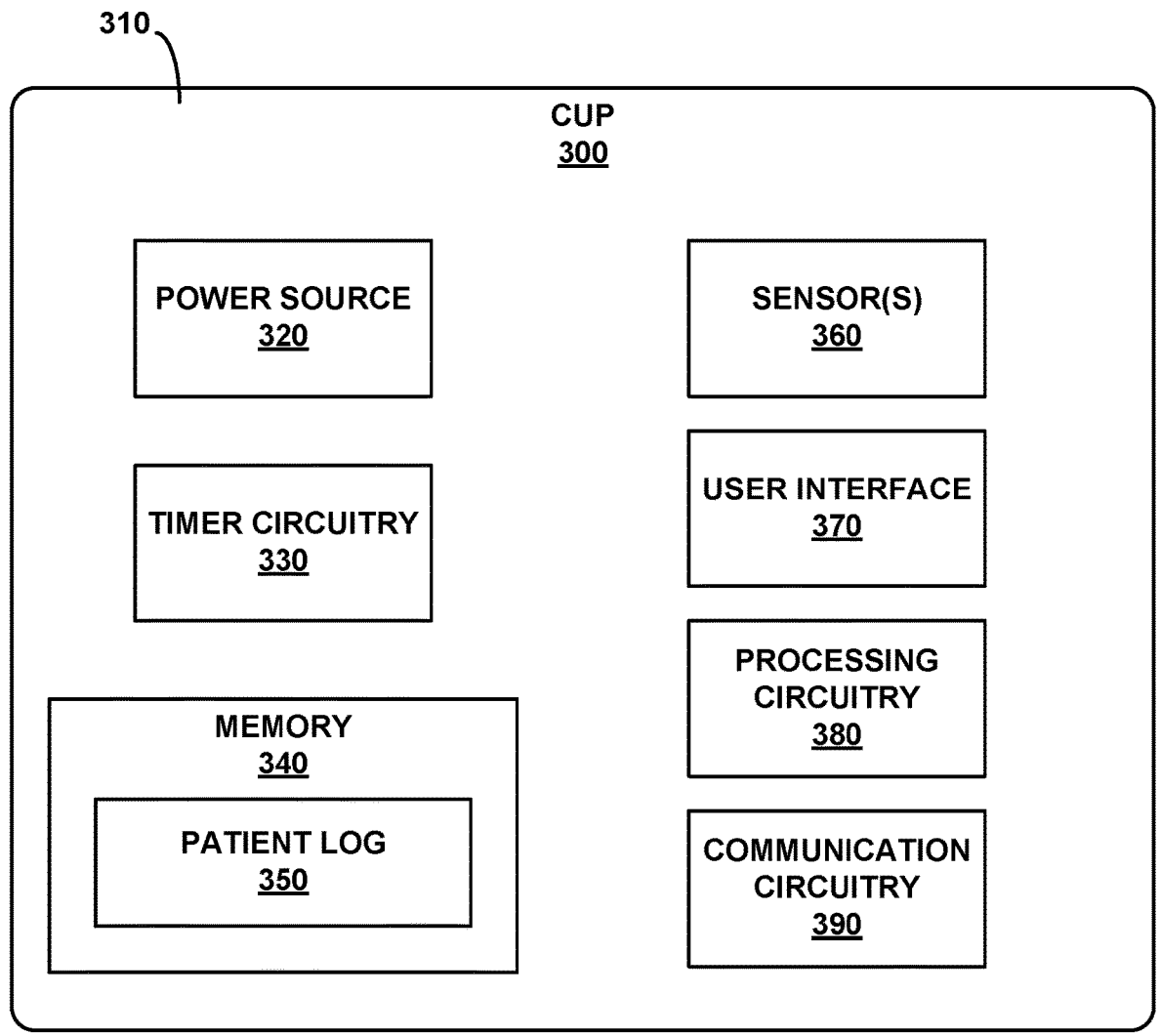
FIG. 3 is a block diagram of the cup of the example system of FIG. 1 to predict a urinary event of a patient according to an example of the techniques of the disclosure.

FIG. 3 is a block diagram of cup 300, which is one example of cup 100 of FIG. 1. As discussed above, cup 300 may be a fluid consumption cup (e.g., a cup for drinking). Cup 300 may comprise a cup body 310. Cup 300 may include a power source 320, timer circuitry 330, a memory 340 that may be configured to store a patient log 350, one or more sensors 360, a user interface 370, processing circuitry 380, and communication circuitry 390. Cup 300 may not necessarily include all of the illustrated elements, in some examples, and may include other elements than those illustrated, in some examples. Cup 300 may comprise a power source and electronic components as described herein (e.g., cup 300 may be considered a smart cup).

Power source 320 delivers operating power to various components of cup 300. Power source 320 may include a small rechargeable or non-rechargeable battery and a power generation circuit to produce the operating power. Recharging may be accomplished through proximal inductive interaction between an external charger and an inductive charging coil within cup 300. Power source 320 may comprise replaceable batteries, in some examples, and cup body 310 may be configured such that a patient (e.g., patient 112 of FIG. 1) may access the cavity where power source 320 is stored to replace the batteries.

Timer circuitry 330 may be configured to transmit a time stamp at the time an event occurs, such as described further herein. In an example, processing circuitry 380 may determine that patient consumes a volume of fluid during a time period. Processing circuitry 380 may control timer circuitry 330 to transmit the times to processing circuitry 380 at which the patient began and finished consuming (e.g., drinking) the fluid from cup 300. Processing circuitry 380 may control memory 340 to update patient log 350 with the time stamp that corresponds to initiating fluid consumption, the time stamp that corresponds to terminating fluid consumption, the amount of fluid consumed during that time period (e.g., the difference in time between starting and ending fluid consumption), the location where the patient drank the fluid, and other information associated with patient behavior or environmental characteristics that occurred or were present during that fluid consumption duration.

Memory 340 may store instructions that cause processing circuitry 380 to provide the functionality described herein, and information used by processing circuitry 380 to provide the functionality ascribed to cup 300 as described herein. Memory 340 may include any volatile, non-volatile, magnetic, optical, or electrical media, such as a random-access memory (RAM), read only memory (ROM), non-volatile RAM (NVRAM), electrically-erasable programmable ROM (EEPROM), flash memory, or any other digital or analog media. Memory 340 may also include a removable memory portion that may be used to provide memory updates or increases in memory capacities. A removable memory may also allow patient data to be easily transferred to another computing device, or to be removed before cup 300 is used to for another purpose (e.g., upgrade the cup body 310 hardware, or for use for another patient).

Patient log 350 may comprise patient information, information about the environment that the patient was in at a particular time, fluid information, patient voiding information, or patient health information. Patient log 350 may comprise information organized in tables, lists, or graphical formats. Patient log 350 may include time stamp information corresponding to events, behavior, or circumstances of the patient. Patient log 350 may include information about the fluid state of the patient (e.g., edema state, hydration levels, perspiration information, or any other type of fluid state information).

Cup 300 may comprise one or more sensors 360. In some examples, sensors 360 may be configured to detect fluid in cup 300. In some examples, sensors 360 may be configured to detect characteristics of fluid in cup 300. In some examples, sensors 360 may be configured to detect the environment where the patient possesses or controls cup 300 (e.g., in a bathroom, at a work office, outside, or at a concert or sporting event). In general, sensors 360 may include one or more sensing elements that sense values of a respective patient or environmental parameter. For example, sensors 360 may include one or more accelerometers, optical sensors, chemical sensors, temperature sensors, pressure sensors, audio sensors (e.g., a microphone), an image sensor (e.g., a camera), an impedance sensor, a pressure sensor, or any other types of sensor. Sensors 360 may output sensed values to processing circuitry 380. Sensors 360 may detect one or more types of signals and transmit the one or more signals to processing circuitry 380, for example.

User interface 370 may be configured or otherwise operable to receive input from a user. User interface 370 may be configured to display information to the user. For example, user interface 370 may comprise one or more lights, a display, a motor configured to provide a vibration alert (e.g., similar to "vibrate" mode on a smartphone), a speaker configured to alert the user of an indication. The patient may interact with user interface 370, which may include display configured to present graphical user interface to the patient, and a keypad or another mechanism for receiving input from the patient.

Processing circuitry 380 may include fixed function processing circuitry or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 380 herein may be embodied as firmware, hardware, software or any combination thereof. Processing circuitry 380 may control other elements in cup 300. In some examples processing circuitry 380 may control other devices (e.g., mobile computing device 104 of FIG. 1).

Communication circuitry 390 includes any suitable hardware, firmware, software, or any combination thereof for communicating with another device (e.g., mobile computing device 104 of FIG. 1 or IMD 106 of FIG. 1). Communication circuitry 390 may be configured to transmit or receive radiofrequency ("RF") signals via an antenna (not shown). Communication circuitry 390 may be configured for RF communication with an external device (e.g., via an antenna). In some examples, communication circuitry 390 comprises input circuitry configured to receive a signal from another device or element of cup 300. In some examples, communication circuitry 390 comprises output circuitry configured to transmit information from cup 300 to another device. For instance, communication circuitry 390 may comprise circuitry configured to transmit fluid consumption information to a mobile computing device.

Communication circuitry 390 may be coupled to an internal antenna or an external antenna. Communication circuitry 390 may also be configured to communicate with another computing device via wireless communication techniques, or direct communication through a wired connection. Examples of local wireless communication techniques that may be employed to facilitate communication between a remote device (e.g., remote device 124 of FIG. 2), cup 300 and another computing device include RF communication according to the 802.11 or Bluetooth specification sets, infrared communication (e.g., according to the IrDA standard), or other standard or proprietary telemetry protocols. An additional computing device in communication with cup 300 may be a networked device such as a server capable of processing information retrieved from IMD 106, a sensor device, or a mobile computing device. Accordingly, communication circuitry 390 may send information to another device or to a network (e.g., network 102 of FIG. 1) on a continuous basis, at periodic intervals, or upon request from cup 300.

Cup body 310 may be different shapes or sizes. In general, cup body 310 may comprise a space to house electronics of cup 300 (e.g., processing circuitry 380 and power source 320). Cup body 310 includes a cavity to house fluid. In some examples cup body 310 is configured to couple to a cover or lid (e.g., a removable cover) configured to keep fluid in cup 300, such as to avoid a spill. In some examples cub body 310 may be insulated, to help maintain fluid temperature. Cup body 310 may be sized to store an amount of fluid. In an example cup body 310 may be configured to store about 320 milliliters (about 5.1 fluid ounces) to about 1200 milliliters (about 40.1 fluid ounces). In an example, cup body 310 may be shaped to fit into a typical car cup-holder. An example of cup body 310 may be an insulated coffee or tea fluid storage body configured to store about 355 milliliters (about 12 fluid ounces) of fluid.

In some examples, a patient may carry cup 300 as a part of daily life. Cup 300, alone and/or in combination with one or more other devices (e.g., sensor device 108 of FIG. 2, mobile computing device 104 of FIG. 2, or remote device 124 of FIG. 2) may be configured to automatically track patient behavior (e.g., activity, voiding, drinking, eating, et cetera), and cup 300 may be configured to atomically store the behavior information in patient log 350. Cup 300 may be configured to determine that a urinary event of the patient is predicted to occur (e.g., the occurrence of the urinary event may be predicted based on the information stored in patient log 350). Cup 300 may provide a notification to the patient that the urinary event is predicted to occur in response to the determination. The patient, having received the notification sufficiently in advance of the predicted urinary event (e.g., the urinary voiding event), may then take measures to ensure the patient is near a toilet or is wearing a diaper when the event is predicted to occur. By automatically updating patient log 350, the patient may avoid having to manually track their fluid consumption and/or fluid state. The patient alone may not be able to reliably determine that a urinary event is predicted to occur. Cup 300 may improve the patient's quality of life, including by offloading the task of tracking urinary voids and fluid consumption.

Cup 300, alone or in combination with any element of FIG. 2, may be configured for predicting a urinary event of a patient (e.g., patient 112). The patient may wear, for example, a sensor device that may be in the form of an activity tracker configured to sense patient activity. For instance, processing circuitry 380 may be configured to receive one or more signals.

One or more sensors (e.g., sensors 360) may detect fluid being removed from cup 300. For example, sensors 360 may comprise an accelerometer that determines acceleration along one or more axis (e.g., in three dimensions). Sensors 360 may transmit one or more signals (e.g., accelerometer signals or fluid flow signals) to communication circuitry 390. Communication circuitry 390 may transmit the accelerometer signals to processing circuitry 380. Processing circuitry 380 may be configured to process the one or more signals. For example, processing circuitry 380 may be configured to determine, based on the one or more signals, that fluid was discarded (e.g., poured out) or consumed by the patient. For example, accelerometer signals having relatively smooth acceleration curves may indicate that the patient is lifting cup 300 to drink, or accelerometer signals that indicate that a top opening of the cup does not pass a threshold angle (e.g., more than a horizontal angle during a minimum duration). In an example, accelerometer signals having that pass a threshold angle in less than a minimum duration may indicate that the patient has dumped fluid from cup 300.

One or more signals (e.g., accelerometer signals, fluid flow signals, or other signals) may be indicative of the rate of volume removal from cup 300. A rate above a threshold may indicate that the patient is throwing fluid out (e.g., discarding down a drain). In contrast, signals of a relatively slow rate may indicate that the patient is drinking the fluid.

Sensors 360 may comprise a temperature sensor. Processing circuitry 380 may determine dumping versus consuming fluid by taking into account the temperature of the fluid. For example, for a relatively hot fluid (e.g., coffee or tea), processing circuitry 380 may use a longer duration (e.g., rate of consumption) to determine that the patient is drinking, because the patient would not drink a hot fluid as fast as a room temperature fluid or a cold fluid. For a room temperature fluid or a cold fluid, for example, processing circuitry 380 may implement more confirmatory steps, because a patient may lift cup 300 and drink the fluid at a similar rate as dumping.

Other types of sensors may be used. A fluid flow sensor may determine the amount of volume being removed from cup 300 over time. In some examples, cup 300 comprises the fluid flow sensor. In some examples, a cover or a lid of cup 300 comprises the fluid flow sensor.

Memory 340 may include template signals (e.g., template accelerometer signals or template fluid flow signals). Processing circuitry 380 may be configured to compare the one or more signals that indicate fluid removal from cup 300 to, for example, a template dumping signal or a template consumption signal. Processing circuitry 380 may be configured to determine multiple confirmatory steps before determining dumping versus consumption. In general, sensors 360 may sense the amount (e.g., volume) of fluid in cup 300. Sensors 360 may sense fluid being removed from cup 300. Processing circuitry 380 may be configured to track volume of fluid in cup 300 over time, and may be configured to determine the amount of fluid the patient consumes over time.

In an example, cup 300 may determine that the patient consumed 8 ounces of a 12-ounce volume of coffee at 9:00 a.m., and discarded 4 ounces of the ounce volume of coffee at 9:15 a.m. Processing circuitry 380 may track when the patient urinates (e.g., at 10:30 a.m.). In some examples, such as by using a fluid voiding cup or voiding system, cup 300 may determine when and how much the patient urinates. Processing circuitry 380 may determine that the patient further consumed a total of 16 ounces of water over the next hour (e.g., the patient partially filled cup 300 with water twice). Processing circuitry 380 may control memory 340 to store this and other information in patient log 350, and based on the updated patient log 350, determine that a predicted urinary voiding event is predicted to occur at 1:00 p.m., for example. Cup 300 and/or mobile computing device 104 of FIG. 1 may provide an indication (e.g., with a warning time) to the patient so that the patient may reach a toilet in time to void.

In some examples, sensors 360 or other sensors described herein may sense the fluid in cup 300. Such sensors may generate one or more signals that indicate the amount of fluid removed from cup 300 and may indicate characteristics of the fluid being removed from cup 300. For example, processing circuitry 380 may determine one or more characteristics of the fluid based on the signals generated by the sensors. Processing circuitry 380 may update patient log 350 based on the one or more characteristics.

In an example, the one or more characteristics may be fluid type (e.g., soda, tea, coffee, water, sports drink, smoothie), whether there are ice cubes in cup 300, fluid temperature, fluid potential of hydrogen (pH) (e.g., acidity), sugar content of the fluid, caffeine content of the fluid, what types of other electrolytes are in the fluid, or any other characteristic of the fluid. In some examples, the sensors described herein may include a camera that may capture a picture of the fluid (either automatically or triggered by the patient), and processing circuitry (e.g., processing circuitry 480 of mobile computing device 404 of FIG. 4) that may determine characteristics of the fluid in cup 300. Processing circuitry 380 may update patient log 350 to include fluid characteristic information, and determining that the urinary event is predicted to occur may be based on the updated patient log 350.

In general, cup 300 may determine any fluid consumed by the patient and any fluid exiting the patient (e.g., fluid in and fluid out over time), and may determine a fluid state of the patient based on the fluid in and fluid out information, such as stored in patient log 350. For example, as described above, processing circuitry 380 may determine an amount of fluid consumed by the patient, including automatically from cup 300. The patient may also update patient log 350, such as via an application on mobile computing device 104 of FIG. 1. In some examples, cup 300 automatically tracks other fluids (e.g., not necessarily from cup 300) and food that the patient consumes, such as via sensor device 108 of FIG. 1 or mobile computing device 104 of FIG. 1.

In some examples, fluid leaving the patient may be in the form of perspiration (e.g., sweating during normal activity due to resting metabolism or during physical activity due exercise). In some examples, fluid leaving the patient may be in the form of voiding (e.g., urinating or defecating). In some examples, fluid leaving the patient may be in the form of expiration (e.g., the moisture during breathing). In some examples, fluid leaving the patient may be in the form of spitting or vomiting. Sensor device 108 of FIG. 1, mobile computing device 104 of FIG. 1, and/or a voiding cup may sense and track any fluid leaving the patient.

In some examples, communication circuitry 390 may receive one or more signals correlated to patient activity. Such patient activity may be any activity described with respect to fluid leaving the patient. In general, physical patient activity may include signals corresponding to heart rate, degree of physical activity (e.g., intensity over time), perspiration (e.g., amount of sweat), or respiration of the patient (e.g., breathing over time). Processing circuitry 380 may update patient log 350 based on the signals correlated to patient activity.

In some examples, communication circuitry 390 is configured to receive one or more signals correlated to fluid leaving the patient, such as patient voiding signals. Processing circuitry 380 may update patient log 350 based on the one or more signals correlated to patient voiding. For example, a microphone (e.g., a microphone of sensors 360 of cup 300 or a microphone of another device, such as a microphone of sensor device 108 or mobile computing device 104 of FIG. 1) may detect that the patient is urinating, and based on the duration of urination, the volume of the splash, and other characteristics of the signal or the patient log, may determine an amount (or estimated amount) of urination. In general, any patient event, such as a voiding event, may be time stamped and stored in patient log 350. Processing circuitry 380 may be configured to update patient log 350 based on the one or more signals correlated to patient voiding.

Processing circuitry 380 may store other information about the patient, as it relates to the fluid state of the patient, in patient log 350. For example, processing circuitry 380 may store a location of the patient in patient log 350. In an example, cup 300 and/or mobile computing device 104 of FIG. 1 may determine a geographic location of the patient (e.g., via a global positioning system or wireless internet). Other location information, such as "in a bathroom," "at work," "at home," "at a sporting event or concert in an arena," "on a hiking trail," or other contextual location information may be stored in patient log 350. Processing circuitry 380 may be configured to receive, such as from a mobile computing device, any location information of the patient, and may be configured to update patient log 350 based on the location. Processing circuitry 380 may determine that the urinary event is predicted to occur based on the location information. In some examples, processing circuitry 380 may increase or decrease the warning time (e.g., the sensitivity) of the indication that the urinary event is predicted to occur based on the location of the patient. For example, if the patient is at popular concert venue that typically has long bathroom wait times, then processing circuitry 380 may provide a more conservative determination that a urinary event is predicted to occur, such as to account for queue lengths, or distance to a toilet. In an example, if the patient is at home, then processing circuitry 380 may provide a less conservative determination (e.g., less of a warning time) that a urinary event is predicted to occur, because the patient likely could reach a bathroom in time.

In some examples, processing circuitry 380 may be configured to determine a fluid state of the patient based on patient log 350, such as over time. Additionally, in some examples, patient log 350 may include patient fluid state information. In an example, if the fluid state of the patient is relatively high, such as due to a high hydration state due to consuming large volumes of fluids, the processing circuitry 380 may determine that a urinary event is predicted to occur based on the fluid state. In an example, processing circuitry 380 may be configured to provide a notification of the patient's fluid state, for receipt by the patient, based on the determine fluid state. This way, the patient may be made aware that they are highly hydrated. In some examples the notification includes other information, such as information based on fluid consumption. For example, if the patient has drunk large amounts of caffeine (e.g., a diuretic), this may mean that a urinary voiding event is more imminent than if the patient had drunk a fluid without a diuretic.

In some examples, processing circuitry 380 may provide a notification (e.g., an instruction), to any combination of the patient, a health care provider, or another device. For example, the instruction may be configured for receipt by a medical device (e.g., medical device 106 of FIG. 1), and may be an instruction to adjust at least one of a neuromodulation program or a mechanical support therapy, such as to address or avoid an incontinence event. In an example, the notification may be an instruction for receipt by a user (e.g., the patient or the heath care provider) to adjust a drug dose. In some examples, processing circuitry 380 provides a notification to the user that the urinary event is predicted to occur at a particular time, or a time window. In some example, processing circuitry 380 provides the probability of occurrence of the future event within the time window.

The techniques and systems may be helpful for patients having a disease state sensitive to fluid intake. For example, the subject matter described herein may allow the patient to live a more normal lifestyle. The patient may not be able to determine a predicted urinary event based on complex inputs for a patient log including those described herein, or may not be able to determine the predicted urinary event in time to take appropriate remedial action.

In some examples, processing circuitry 380 updates patient log 350 based on one or more signals (e.g., a signal that indicates an amount of fluid removed from cup 300, a signal about patient behavior, a signal about patient location, or other signals). In some examples, processing circuitry 380 determines that a urinary event is predicted to occur based on the updated patient log. In some examples, processing circuitry 380 employs machine learning to better make such a determination. In some examples, processing circuitry 380 provides a notification that the urinary event is predicted to occur.

Processing circuitry 380 may update patient log 350 with the perspiration information. In some examples processing circuitry 380 may be configured to determine a fluid state of the patient based on patient log 350. The fluid state may include an estimate of the patient's hydration level. For example, if the patient has consumed a relatively large amount of fluid in a relatively short amount of time, their fluid state may be relatively high. Cup 300 may be configured to determine how much activity or perspiration the patient has had in a period of time. For a patient that has had a relatively high amount of perspiration relative to a smaller amount of fluid consumption, then the patient's fluid state may be relatively lower. In an example, if the patient is doing high intensity cardio exercise, Cup 300 may determine that the amount of time to the next predicted void may be delayed due to perspiration. In some examples, these techniques allow for differentiation between stress incontinence and urge incontinence episodes, such that the two types can be predicted using separate techniques (e.g., algorithms).

The fluid state of the patient may be stored in patient log 350. Processing circuitry 380 may be configured to provide a notification of the patient's fluid state, for receipt by the patient, based on a determined fluid state of the patient. In some examples the patient fluid state may be indicated relatively simply via user interface 370. For example, three lights (e.g., LED lights, such as one red, one yellow, one green) may indicate a relative high, medium, and low fluid states, so that the patient may have a general idea how close in time to a urinary void may be.

Cup 300 may be configured to automatically track symptoms of the patient over time. In an example, patient log 350 may be configured to track patient symptoms (e.g., time stamped incontinence episodes such as leaks, voids, or urgency episodes, as well as the severity of the urge. Cup 300, sensor device 108 of FIG. 1, and mobile computing device 104 of FIG. 1 may work in conjunction to track the patient's symptoms. The symptoms may be included in patient log 350, along with fluid intake, for example. In some examples, symptoms may be entered manually by the patient or a caregiver. In some examples, symptoms may be tracked automatically via sensors (such as sound of voiding or toilet flushing, vicinity to a known bathroom location via any of the devices described herein), or prompted by sensors and confirmed by the patient. For example, the mobile computing device may determine, via a microphone sensor, that the patient is urinating due to the sound of urine splashing into the toilet. Mobile computing device 104 may prompt the patient to confirm that the patient urinated (e.g., with a notification on the screen of the mobile computing device). The mobile computing device may then update patient log 350 with the void information. In some examples, a fluid intake sensor (e.g., such as apart of cup 300) may work in conjunction with a voiding sensor (e.g., the microphone sensor) to track patient symptoms.

In some examples, cup 300, mobile computing device 104 of FIG. 1, and/or remote device 124 of FIG. 2 may comprise a machine learning algorithm configured to learn the patient's fluid-symptom pattern and predict potential symptom onset based on the patient's real-time fluid intake, taking into account the patient's hydration level based on previous fluid intake and voiding, the types of fluids ingested, patient's circadian rhythm, and activity level, among other the patient or environmental characteristics. User interface 370 may provide warning to the patient such that it allows the patient sufficient time to plan for a void and prevents an incontinence or urge episode. The patient may program and adjust the desired warning time. In some examples, processing circuitry 380 automatically increases the warning time depending on the patient's fluid state or environmental circumstances (e.g., time or distance to a toilet).

The machine learning algorithm (e.g., a machine learning model) may also take into account psychological or other contextual input based on patient's stress level or geographical location information. For example, stress level may be detected via heart rate, breathing, or sweat level via another wearable sensor (e.g., sensor device 108 of FIG. 1). Geographical information may help automatically adjust sensitivity or specificity of the algorithm according to historical experience, such as stored in patient log 350. For example, if the patient tends to have more symptoms at a specific location due to heightened stress level or limited bathroom access, the algorithm may automatically provide more conservative warning when sensing the device being in that location.

In some examples, because stress incontinence may be associated with a different set of warning time and patient coping methods, the algorithm may track stress incontinence episodes separately and provide a different type of warning for stress incontinence episodes. For example, a warning for potential stress incontinence episode may be provided when the patient activity level is high and the patient is well hydrated above certain threshold.

In some examples, the systems and techniques described herein include providing an indication, such as may include an instruction for receipt by the medical device to adjust a therapy. For example, the instruction may comprise adjusting a neuromodulation program or a mechanical support therapy. In some examples, the indication comprises an instruction to adjust a drug dose.

For example, upon determining a predicted symptom onset, processing circuitry 380 may also control the medical device to trigger therapy adjustment. In an example, electrical neuromodulation therapy may be adjusted to a higher intensity or a different frequency to elicit additional bladder inhibition effect or temporary sphincter contraction. In an example, oral drug dosing may be increased if a certain number of increased warnings per week are detected. Therapy titration or programming may be executed locally via telemetry, or executed via network 102 of FIG. 1 (e.g., cloud infrastructure) and confirmed by a healthcare provider.

In the following descriptions with respect to mobile computing device 404 (FIG. 4) which is one example of mobile computing device 104 of FIG. 1, medical device 506 (FIG. 5) which is one example of medical device 106 of FIG. 1, sensor device 108 of FIG. 1, and remote device 124 of FIG. 2, each device may comprise elements that correspond to a respective element of cup 300. For example, as described herein, each of these devices may comprise processing circuitry configured to carry out the techniques described herein. Any one or combination of the processing circuitry of the respective device may carry out the techniques described herein. As an example, processing circuitry 480 of mobile computing device 404 may be configured to perform the same or similar tasks as processing circuitry 380 of cup 300 as described herein. In some examples, data is transmitted from cup 300 or sensor device 108 of FIG. 1 to mobile computing device 404 of FIG. 4, and processing circuitry 480 performs the techniques described herein. Similarly, although not shown, sensor device 108 and remote device 124, as shown in FIG. 1, may each comprise processing circuitry that may be configured to perform the same or similar tasks as processing circuitry 380 of cup 300 as described herein. Likewise, power source 420 of mobile computing device 404 of FIG. 4 may generally be configured similarly as power source 320 of cup 300. In an example, the patient log described herein may be stored on memories of one or any combination of elements. For example, patient log 350 may comprise the same data as patient log 450 and patient log 550. In general, to carry out the techniques described herein, any element of cup 100 may be similarly implemented on another element of system 114. For example, although not shown, the patient log may be stored securely on remote device 124 or elsewhere.

Figure 4:
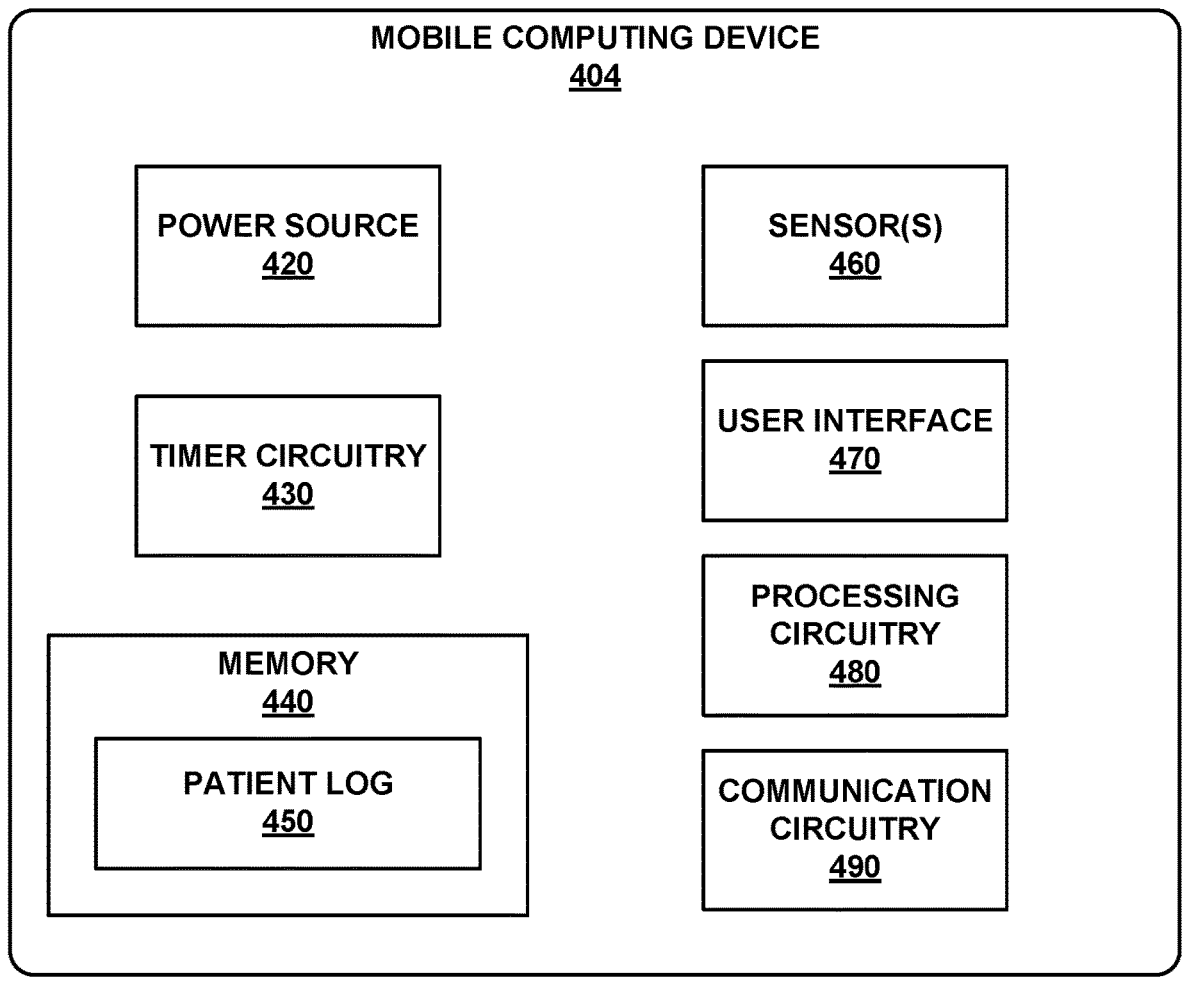
FIG. 4 is a block diagram of the mobile computing device of the example system FIG. 1 to predict a urinary event of a patient according to an example of the techniques of the disclosure.

FIG. 4 is a block diagram of mobile computing device 404, which is one example of mobile computing device 104 of the example system 114 of FIG. 1. In some examples, mobile computing device 404 may include a power source 420, timer circuitry 430, a memory 440 that may be configured to store a patient log 450, one or more sensors 460, a user interface 470, processing circuitry 480, and communication circuitry 490. As described above, each of the elements of mobile computing device 404 may correspond to and have the same or similar functionality of the respective elements of cup 300. Mobile computing device 404 may comprise a mobile cellular telephone (e.g., a smartphone), that may be configured to communicate with other devices via communication circuitry 490, and may have a relatively larger display, such as a touch screen.

Figure 5:
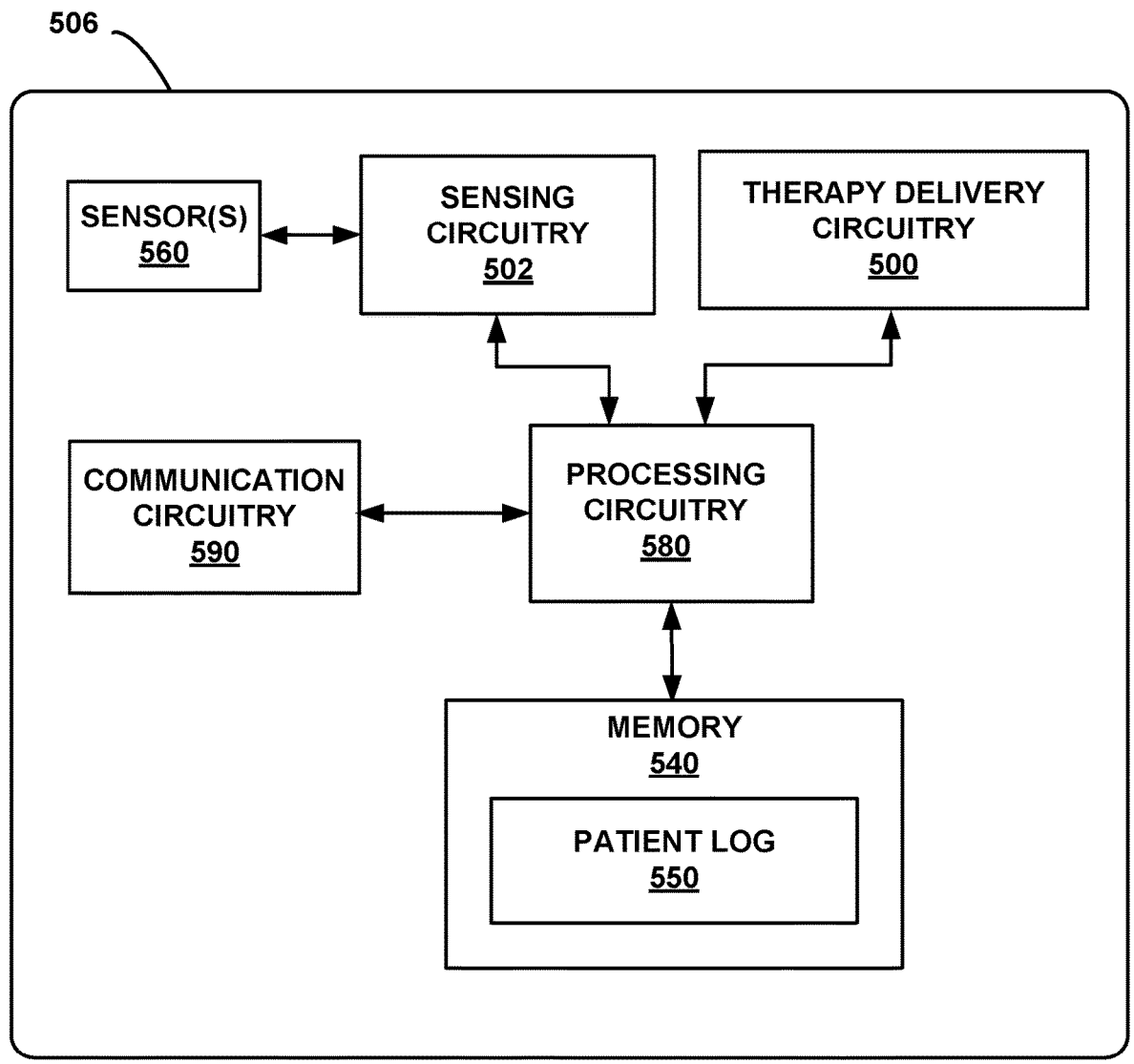
FIG. 5 is a block diagram of the medical device of the example system FIG. 1 to predict a urinary event of a patient according to an example of the techniques of the disclosure.

FIG. 5 is a block diagram of medical device 506, which is one example of medical device 106 of the example system 114 shown in FIG. 1. In an example, medical device 506 may comprise an implantable medical device, such as a neurostimulator. In an example, although not shown, medical device 506 may comprise a mechanical support device for urinary incontinence. Medical device 506 may comprise processing circuitry 580 (e.g., that may comprise the same or similar functionality as processing circuitry 380), memory 540 that may be configured to store a patient log 550, one or more sensors 560, therapy delivery circuitry 500, sensing circuitry 502, and communication circuitry 590.

In the example shown in FIG. 5, memory 540 may be configured to store therapy programs. Each stored therapy program may define a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

As described herein, medical device 506 may be external or implanted, and may be used to deliver electrical stimulation therapy to a patient (e.g., patient 112) to various tissue sites to treat a variety of symptoms or conditions such as chronic pain, tremor, Parkinson's disease, epilepsy, urinary or fecal incontinence, sexual dysfunction, obesity, or gastroparesis. Medical device 506 may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

In some examples, a sensor device (e.g., sensor device 108 of FIG. 1) may comprise a wearable sensor device. In some examples, the sensor device may be configured to sense patient or environment signals. For example, the sensor device may be configured to detect audio or images from the environment of the patient. In an example, a sensor device may comprise one or more accelerometers, and may be configured to track the patient's activity level and other patient activity (e.g., coughing, laughing, sneezing, or jumping).

In some examples, the sensor device may comprise an accelerometer, a bonded piezoelectric crystal, a mercury switch, or a gyro. In some examples, sensor device may provide a signal that indicates a physiological parameter of the patient, which in turn varies as a function of patient activity. For example, the device may monitor a signal that indicates the heart rate, electrocardiogram (ECG) morphology, electroencephalogram (EEG) morphology, respiration rate, respiratory volume, core temperature, subcutaneous temperature, or muscular activity of the patient.

In some examples, the sensor device may be configured to generate a signal both as a function of patient activity and patient posture. For example, accelerometers, gyros, or magnetometers may generate signals that indicate both the activity and the posture of the patient.

An accelerometer may be a 3-axis accelerometer configured output a signal for each of the x, y, and z axis. In some examples, sensor device 108 may detect the patient posture state via multiple single-axis accelerometers, dual-axis accelerometers, 3-axis accelerometers, or some combination thereof, or may include a sensor other than an accelerometer. In the case of a 3-axis accelerometer, posture sensor data may include a signal value sampled from the output signal for each axis generated by the accelerometer. In some examples, the signal value for one or more of the axes may be an average value determined based on a plurality of sampled signal values. Additionally or alternatively, posture sensor data may include a magnitude and/or angle of a posture vector derived from the values of each axis of the accelerometer sensor within a 3-dimensional vector space. Example accelerometers may include a micro-electro-mechanical system (MEMS)-based accelerometer.

Figure 6:
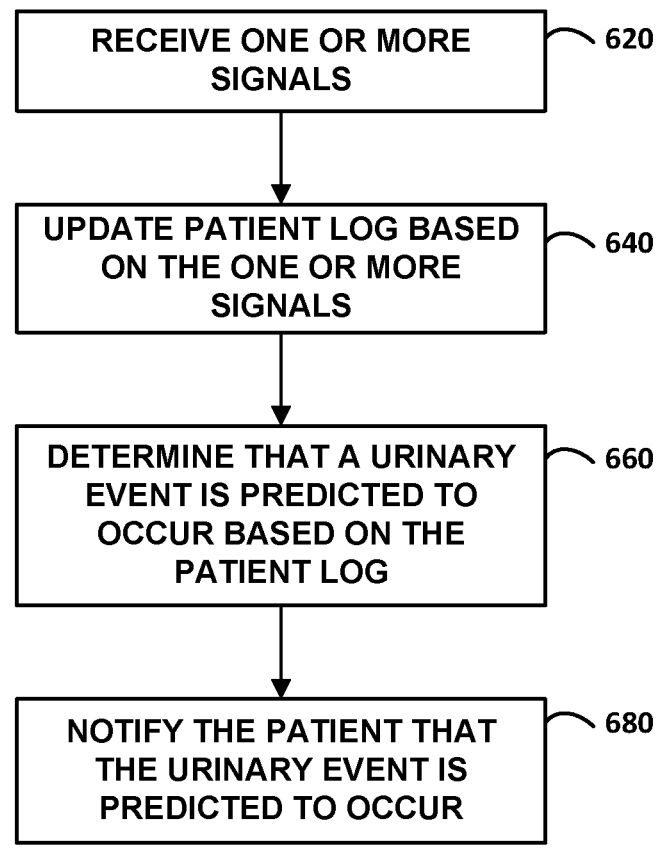
FIG. 6 is a flowchart illustrating an example of providing an indication that a urinary event is predicted to occur according to an example of the techniques of the disclosure.

FIG. 6 is a flowchart illustrating an example of providing an indication that a urinary event is predicted to occur according to an example of the techniques of the disclosure. The techniques of FIG. 6 are described as being performed by mobile computing device 104 of FIG. 1 and/or mobile computing device 404 of FIG. 4. However, in other examples, other computing devices may perform some or all of the techniques of FIG. 6, such as remote device 124 of FIG. 2.

Mobile computing device 104 may receive one or more signals indicative of an amount (e.g., a volume) of fluid removed from a fluid consumption cup (e.g., cup 100) (620). For instance, processing circuitry 480 may receive the one or more signals from fluid consumption cup 100 of FIG. 1 that indicate, for example, that the patient has consumed 300 milliliters of fluid. For example, sensors within cup 100 may be configured to determine that the 300 milliliters of fluid were consumed, and a remaining amount of fluid was discarded from cup 100 without being consumed (e.g., hot coffee became cold, and the patient dumped the remaining cold coffee out).

Mobile computing device 104 may update a patient log (e.g., any one or combination of patient logs described herein) (640). For instance, processing circuitry 480 may update patient log 450 to indicate that the patient had consumed the 300 milliliters of fluid at a particular time. In some examples, one or more additional devices, such as remote device 124 of FIG. 2, may participate in the updating the patient log. For instance, to update the patient log, mobile computing device 104 may forward a representation of the signals received and/or a copy of some or all of the patient log to remote device 124 of FIG. 2.

Mobile computing device 104 may determine that a urinary event of the patient is predicted to occur based on the patient log (e.g., based on the updated patient log) (660). For instance, processing circuitry 480 may determine that the urinary event is predicted to occur based on patient log 450. Processing circuitry 480 may determine, based on for example, an increase in the patient's fluid state past a threshold due to the 300 milliliters, that the patient is predicted to have a urinary event within 15 minutes. For example, if the patient had previously consumed relatively larger amounts of fluid (e.g., 1 liter or 2 liters of water in a period of time), then processing circuitry 480 may determine that the 300 milliliters crosses a threshold for a particular duration.

In some examples, mobile computing device 104 may determine that the urinary event is predicted to occur based on a message received from another device. For instance, mobile computing device 104 may determine that the urinary event is predicted to occur at a particular time in response to receiving a message from remote device 124 of FIG. 2 that indicates that the urinary event is predicted to occur at the particular time.

In some examples, the prediction of the urinary event may be performed with the use of a machine learning model trained based on a fluid consumption history and a voiding history of the patient. For instance, mobile computing device 104 and/or remote device 124 of FIG. 2 may provide the patient log to the machine learning model, when may output an indication of a predicted event, Mobile computing device 104 may provide an indication (e.g., a notification) that the urinary event is predicted to occur (680). For instance, processing circuitry 480 and/or user interface 470 may provide the indication to the patient that the urinary event is predicted to occur. The indication may comprise a flashing light, for example. The indication may, in some examples, comprise an information pop-up on a display that has information, such as "fluid state: high/predicted urinary voiding event: within 15 minutes." The time at which mobile computing device 104 outputs the notification may be based on the determined amount of warning time and the patient log. For example, mobile computing device 104 may output the notification where determining that a time difference between a current time and a time at which the urinary voiding event is predicted to occur is less than the warning time. In an example, the preferred warning time can be adjusted by the patient or a clinician. In an example, the estimated time to next episode may be displayed. In an example, the probability of an episode occurrence within a warning time window may be displayed and an alert may be sent if the probability exceeds a set threshold (e.g., alert when there is an 80% or greater chance that an episode will occur in the next 15 minutes.) For instance, if the voiding event is predicted to occur in 20 minutes and the warning time is 15 minutes, mobile computing device 104 may refrain from issuing the warning until the 15 minutes from the voiding event. As such, while a voiding event may be predicted in the future of the patient (i.e., the patient is always going to have to urinate at some point in the future), mobile computing device 104 may refrain from outputting unnecessary warnings.

By automatically providing the patient with a notification that an event is predicted to occur, the techniques of this disclosure enable the patient to take action based on the notification. For example, the patient may determine that, to avoid a leak, they should seek a toilet.

Figure 7:
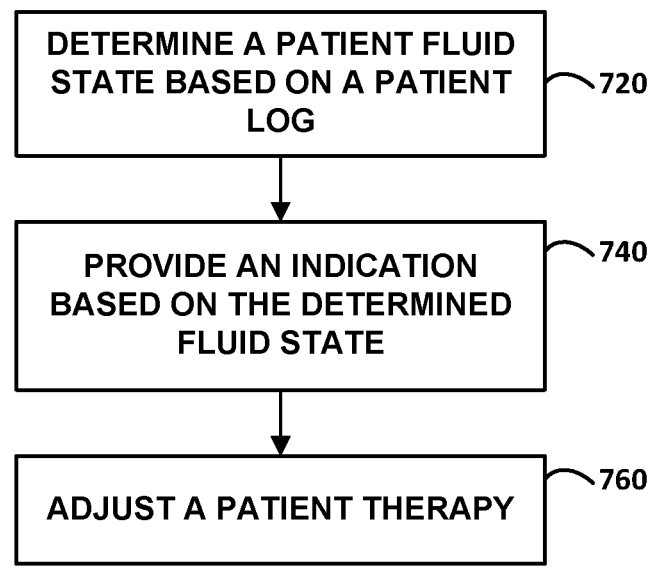
FIG. 7 is a flowchart illustrating an example of adjusting a therapy according to an example of the techniques of the disclosure.

FIG. 7 is a flowchart illustrating an example of adjusting a therapy according to an example of the techniques of the disclosure. The techniques of FIG. 7 are described as being performed by mobile computing device 104 of FIG. 1 and/or mobile computing device 404 of FIG. 4. However, in other examples, other computing devices may perform some or all of the techniques of FIG. 7, such as remote device 124 of FIG. 2.

Mobile computing device 104 may determine a patient fluid state based on a patient log (720). For instance, processing circuitry 480 may determine the patient fluid state based on patient log 450. The fluid state may be an edema state, a quantitative measure of fluid in the patient relative to historical measurements, or an estimate fluid state based on, for example, fluid in versus fluid out.

Mobile computing device 104 may provide an indication based on the determined fluid state (740). For instance, processing circuitry 480 and/or user interface 470 may provide the indication based on the determined fluid state. For example, the indication may be a number on a display. The indication may be that the fluid state is in a "high" state (relative to "medium" or "low" states), such that the patient may determine that they should urinate within an amount of time (e.g., a buffer time or a warning time).

In some examples, based on the indication, mobile computing device 104 may adjust a therapy (760). For instance, processing circuitry 480 may adjust a therapy automatically in response to the determined fluid state, such as controlling medical device 506 to provide a more appropriate therapy. In some examples, the indication may be an instruction for the patient or a health care provider to adjust a therapy, such as a drug dosage. The examples of techniques in this disclosure may be combined in any combination or permutation.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A system for predicting a urinary event of a patient, the system comprising:
a fluid consumption cup comprising one or more sensors;
communication circuitry configured to receive, from the fluid consumption cup, one or more signals that indicate an amount of fluid removed from the fluid consumption cup; and
processing circuitry configured to:
update a patient log based on the one or more signals that indicate the amount of fluid removed from the fluid consumption cup;
determine that the urinary event is predicted to occur, the occurrence of the urinary event predicted based on the patient log; and
provide, in response to the determination and for receipt by the patient, a notification that the urinary event is predicted to occur.

2. The system of claim 1, wherein the processing circuitry is configured to:
determine, based on the one or more signals that indicate the amount of fluid removed, an amount of fluid consumed by the patient from the fluid consumption cup, and wherein, to update the patient log, the processing circuitry is configured to:
update the patient log based on the amount of fluid consumed by the patient from the fluid consumption cup.

3. The system of claim 2, wherein the processing circuitry is configured to:
determine, based on the one or more signals that indicate the amount of fluid removed, an amount of fluid discarded from the fluid consumption cup without being consumed by the patient, wherein, to determine the amount of fluid consumed by the patient from the fluid consumption cup, the processing circuitry is configured to:
determine the amount of fluid consumed by the patient as the amount of fluid removed from the fluid consumption cup less the amount of fluid discarded from the fluid consumption cup without being consumed by the patient.

4. The system of claim 1, wherein the processing circuitry is configured to determine, based on the one or more signals that indicate the amount of fluid removed, one or more characteristics of the fluid removed from the fluid consumption cup, and wherein processing circuitry is configured to update the patient log based on the on the one or more characteristics.

5. The system of claim 4, wherein the one or more characteristics of the fluid comprise one or more of: fluid type, fluid acidity, sugar content, and caffeine content.

6. The system of claim 1, wherein the communication circuitry is configured to receive one or more signals correlated to patient activity, wherein the one or more signals correlated to patient activity comprise a physical activity indicative of at least one of heart rate, physical movement of the patient, perspiration, or respiration, and wherein the processing circuitry is configured to further update the patient log based on the one or more signals correlated to patient activity.

7. The system of claim 1, wherein the processing circuitry is configured to determine a fluid state of the patient based on the patient log, and wherein the processing circuitry is configured to provide a notification of the fluid state of the patient, for receipt by the patient, based on the determined fluid state.

8. The system of claim 7, wherein processing circuitry is configured to provide an additional notification, for receipt by a health care provider, that the urinary event is predicted to occur.

9. The system of claim 1, wherein the communication circuitry is configured to receive one or more signals correlated to patient voiding, experiencing urgency or urinary incontinence, and wherein the processing circuitry is configured to update the patient log based on the one or more signals correlated to patient voiding, urgency, and urinary incontinence.

10. The system of claim 1, wherein the communication circuitry is configured to receive, from a mobile computing device, a location of the patient, and wherein the processing circuitry is configured to update the patient log based on the location of the patient.

11. The system of claim 1, wherein, to predict the occurrence of the urinary event, the processing circuitry is configured to:
predict, using a machine learning model trained based on a fluid consumption history and a voiding history of the patient, the occurrence of the urinary event based on the patient log.

12. A method for predicting a urinary event of a patient, the method comprising:
receiving, by one or more processors of a system, one or more signals correlated to fluid removal from a fluid consumption cup used by the patient;
updating, by the one or more processors, a patient log based on the one or more signals correlated to fluid removal;
determining, by the one or more processors, that a urinary event for the patient is predicted to occur based on the patient log; and
automatically outputting, for receipt by the patient, an indication that the urinary event is predicted to occur.

13. The method of claim 12, further comprising determining, by the one or more processors and based on the one or more signals correlated to fluid removal, an amount of fluid consumed by the patient from the fluid consumption cup; and updating, by the one or more processors, the patient log based on the amount of fluid consumed by the patient from the fluid consumption cup.

14. The method of claim 13, further comprising determining, by the one or more processors and based on the one or more signals correlated to fluid removal, an amount of fluid discarded from the fluid consumption cup without being consumed by the patient; and
determining, by the one or more processors, the amount of fluid consumed by the patient as the amount of fluid removed from the fluid consumption cup less the amount of fluid discarded from the fluid consumption cup without being consumed by the patient.

15. The method of claim 12, further comprising determining, by the one or more processors and based on the one or more signals correlated to fluid removal, one or more characteristics of the fluid removed from the fluid consumption cup; and updating the patient log based on the on the one or more characteristics.

16. The method of claim 15, wherein the one or more characteristics of the fluid comprise one or more of: fluid type, fluid acidity, sugar content, and caffeine content.

17. The method of claim 12, further comprising receiving, by the one or more processors, one or more signals correlated to patient activity, wherein the one or more signals correlated to patient activity comprise a physical activity indicative of at least one of heart rate, physical movement of the patient, perspiration, or respiration; and
updating, by the one or more processors, the patient log based on the one or more signals correlated to patient activity.

18. The method of claim 12, further comprising determining a fluid state of the patient based on the patient log; and
automatically outputting, for receipt by the patient, an indication of the patient's fluid state based on the determined fluid state.

19. The method of claim 12, wherein the indication comprises an instruction, for receipt by a medical device, to adjust at least one of a neuromodulation program or mechanical support therapy.

20. The method of claim 12, further comprising:
receiving, by the one or more processors, one or more signals correlated to patient voiding; and
updating the patient log based on the one or more signals correlated to patient voiding.

21. The method of claim 12, further comprising:
receiving information about a location of the patient; and
updating the patient log based on the information about the patient.

22. The method of claim 12, further comprising:
predicting, by a machine learning model trained on a fluid consumption history and a voiding history of the patient, the occurrence of the urinary event based on the patient log.

23. A fluid consumption cup comprising:
one or more sensors configured to sense fluid removal from the fluid consumption cup; and
processing circuitry configured to:
determine, based on signals generated by the one or more sensors, an amount of fluid consumed by a patient;
determine an occurrence of a urinary event of the patient predicted based on the amount of fluid consumed by the patient; and output, based on a time difference between a current time and a time at which the urinary event is predicted to occur, a notification of the urinary event.

24. The fluid consumption cup of claim 23, wherein, to determine the amount of fluid consumed by the patient, the processing circuitry is configured to:
- determine, based on the signals generated by the one or more sensors, an amount of fluid removed from the fluid consumption cup;
- determine an amount of fluid discarded from the fluid consumption cup; and
- determine, based on a difference between the amount of fluid removed from the fluid consumption cup and the amount of fluid discarded from the fluid consumption cup, the amount of fluid consumed by the patient.

25. The fluid consumption cup of claim 23, further comprising:
- communication circuitry configured to communicated with an external device, wherein, to determine the occurrence of the urinary event of the patient, the processing circuitry is configured to:
- receive, via the communication circuitry and from the external device, a representation of the time at which the urinary event is predicted to occur.

26. The fluid consumption cup of claim 23, wherein to output the notification, the processing circuitry is configured to:
- output the notification in response to determining that the time difference between the current time and the time at which the urinary event is predicted to occur is less than a warning time.

27. A mobile computing device for predicting a urinary event of a patient, the mobile computing device comprising:
- communication circuitry configured to receive, from a fluid consumption cup, one or more signals correlated to a patient's fluid state;
- processing circuitry configured to:
  - determine the fluid state of the patient based on the one or more signals;
  - update a patient log based on the determined fluid state;
  - determine that the urinary event is predicted to occur based on the patient log; and
  - provide an indication that the urinary void is predicted to occur in response to the determination.

28. The mobile computing device of claim 27, further comprising one or more sensors configured to sense information about the patient, and wherein the processing circuitry is configured to update the patient log based on the information about the patient.

29. The mobile computing device of claim 28, wherein the processing circuitry is configured to determine, in response to the sensed information about the patient, information including one or more of: a fluid type that the patient consumes, a location of the patient, or an activity state of the patient.

30. The mobile computing device of claim 27, wherein the indication comprises a warning, for receipt by the patient, that the urinary void is predicted to occur.

* * * * *